(12) United States Patent
Chia et al.

(10) Patent No.: US 11,737,825 B2
(45) Date of Patent: *Aug. 29, 2023

(54) MEDICAL LASER FIBER

(71) Applicant: Boston Scientific Scimed, Inc., Maple Grove, MN (US)

(72) Inventors: Wen-Jui Ray Chia, Sunnyvale, CA (US); Steven Yihlih Peng, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/243,936

(22) Filed: Apr. 29, 2021

(65) Prior Publication Data

US 2021/0244471 A1  Aug. 12, 2021

Related U.S. Application Data

(63) Continuation of application No. 16/185,392, filed on Nov. 9, 2018, now Pat. No. 11,007,011.

(Continued)

(51) Int. Cl.
*A61B 18/24* (2006.01)
*A61N 5/06* (2006.01)
(Continued)

(52) U.S. Cl.
CPC ............. *A61B 18/24* (2013.01); *A61B 18/22* (2013.01); *A61N 5/0601* (2013.01);
(Continued)

(58) Field of Classification Search
CPC .................... A61B 18/24; A61B 18/22; A61B 2018/00136; A61B 2018/00148;
(Continued)

(56) References Cited

U.S. PATENT DOCUMENTS

2006/0147168 A1  7/2006  DeMartino et al.
2008/0172037 A1  7/2008  Huang et al.
(Continued)

FOREIGN PATENT DOCUMENTS

CN          2697669 Y     5/2005
CN        101458375 A     6/2009
(Continued)

OTHER PUBLICATIONS

Office Action in Chinese Patent Application No. 201880072946.5, dated Feb. 27, 2023 (7 pages).
(Continued)

*Primary Examiner* — Paula J Stice
(74) *Attorney, Agent, or Firm* — Bookoff McAndrews, PLLC

(57) ABSTRACT

One described aspect is an optical fiber comprising: a fiber core that extends along a fiber axis, is configured to transmit a laser energy along the fiber axis, and terminates at a distal end; a first cladding that extends along the fiber axis, is adjacent to the fiber core, and terminates at a distal end; a coating that extends along the fiber axis and terminates at a distal end, wherein the coating is a gold coating; a second cladding that surrounds a portion of the gold coating along the fiber axis, and terminates at a distal end; an outer jacket that extends along the fiber axis and terminates at a distal end; and a fiber tip. Associated laser systems are also disclosed.

19 Claims, 3 Drawing Sheets

Related U.S. Application Data

(60) Provisional application No. 62/584,292, filed on Nov. 10, 2017.

(51) Int. Cl.
  *A61B 18/22* (2006.01)
  *G02B 6/036* (2006.01)
  *G02B 6/02* (2006.01)
  *A61N 5/067* (2006.01)
  *A61B 18/00* (2006.01)

(52) U.S. Cl.
  CPC ..... *G02B 6/02395* (2013.01); *G02B 6/03694* (2013.01); *A61B 2018/00136* (2013.01); *A61B 2018/00148* (2013.01); *A61B 2018/2233* (2013.01); *A61B 2018/2244* (2013.01); *A61B 2018/2266* (2013.01); *A61B 2018/2288* (2013.01); *A61N 5/067* (2021.08); *A61N 2005/063* (2013.01)

(58) Field of Classification Search
  CPC .... A61B 2018/2233; A61B 2018/2244; A61B 2018/2266; A61B 2018/2288; A61N 5/0601; A61N 5/067; A61N 2005/063; G02B 6/02395; G02B 6/03694
  See application file for complete search history.

(56) References Cited

U.S. PATENT DOCUMENTS

| | | |
|---|---|---|
| 2008/0192778 A1 | 8/2008 | Ohsono et al. |
| 2012/0022424 A1 | 1/2012 | Yamamoto et al. |
| 2013/0096545 A1 | 4/2013 | Laudenslager et al. |
| 2014/0107630 A1* | 4/2014 | Yeik .................. A61F 9/008 606/5 |
| 2014/0155948 A1 | 6/2014 | Walsh et al. |
| 2016/0367836 A1* | 12/2016 | Kampasi .............. G02B 6/0008 |
| 2017/0121221 A1 | 5/2017 | Miyamoto |
| 2017/0232161 A1 | 8/2017 | Fewkes et al. |
| 2018/0360629 A1 | 12/2018 | Bernard et al. |

FOREIGN PATENT DOCUMENTS

| | | |
|---|---|---|
| CN | 203422509 U | 2/2014 |
| EP | 2 392 287 A1 | 12/2011 |
| WO | 8201365 A1 | 4/1982 |

OTHER PUBLICATIONS

International Search Report on Patentability and Written Opinion issued in International Application No. PCT/US2018/059992, dated Feb. 28, 2019 (12 pages).

* cited by examiner

MEDICAL LASER FIBER

CROSS-REFERENCE TO RELATED APPLICATIONS

This patent application is a continuation under 37 CFR § 1.53(b) of U.S. application Ser. No. 16/185,392, filed Nov. 9, 2018, which claims the benefit of priority under 35 U.S.C. § 119 to U.S. Provisional Patent Application No. 62/584,292, filed Nov. 10, 2017, each of which is herein incorporated by reference in its entirety.

TECHNICAL FIELD

Various aspects of the present disclosure relate generally to optical fibers and associated laser systems. More specifically, the present disclosure relates to medical laser devices for transmitting laser energy through a fiber.

BACKGROUND

Optical fibers may be used in medical laser systems to deliver a laser energy to a treatment site. Lasers have been used in, for example, urology, neurology, otorhinolaryngology, general anesthetic ophthalmology, dentistry, gastroenterology, cardiology, gynecology, thoracic, and orthopedic procedures. One example of a procedure that may be performed using a laser system is embolization of blood vessels using a microcatheter. Embolization of blood vessels involves inserting a catheter into a primary artery and advancing the catheter to a blood vessel or other area where the blood supply needs to be blocked. A laser may be used to clot and/or form a blockage at the targeted blood vessel or other area. In an embolization procedure, often maneuvering the catheter through the patient's body to the treatment site requires several sharp turns through the torturous vascular pathways. To navigate the vascular pathways, microcatheters are often used in embolization procedures and require strong turn-for-turn torque response. A smaller kink radius and smaller catheter diameter are required for the microcatheters used in embolization procedures compared to traditional catheters. Due to the tight kink radius and small diameter lumen required to complete procedures such as vascular embolization, microcatheters need to be stiff enough to prevent kinking yet flexible enough to navigate tortuous vascular pathways. These requirements present challenges for using microcatheters in combination with laser fibers for embolization or other procedures.

Conventional laser fiber construction consisting of a series of layers including an un-doped glass core, fluorinated glass cladding, polymer cladding and an outer jacket. Typically, conventional laser fibers have a bend radius of approximately 8 mm due to leaking laser energy through the bend and have diminished laser transmission with tight bends in the fiber. As described above, many procedures require laser fibers to have a tight kink radius and small diameter, while maintaining an effective transmission level.

The devices and methods of the current disclosure may rectify some of the deficiencies described above, or address other aspects of the prior art.

SUMMARY

Examples of the present disclosure relate to, among other things, medical laser devices. Each of the examples disclosed herein may include one or more of the features described in connection with any of the other disclosed examples.

In one example, a laser delivery device may include a fiber core that extends along a fiber axis. The fiber core may be configured to transmit a laser energy along the fiber axis and may terminate at a distal end. The device may further include a first cladding that extends along the fiber axis, is adjacent to the fiber core, and terminates at a distal end. The device may also include a coating that extends along the fiber axis and terminates at a distal end. The coating may be a gold coating. The device may further include a second cladding that surrounds a portion of the coating along the fiber axis, and terminates at a distal end. The device may also include an outer jacket that extends along the fiber axis and terminates at a distal end. Also, the device may include a fiber tip.

In a further example, a laser delivery device may include a connector portion at a proximal end of the laser delivery device and an optical fiber connecting the connector portion to a distal end of the laser delivery device. The optical fiber may include a fiber core that extends along a fiber axis. The fiber core may be configured to transmit a laser energy along the fiber axis and may terminate at a distal end. The optical fiber may also include a first cladding that extends along the fiber axis. The first cladding may be adjacent to the fiber core and may terminate at a distal end. The optical fiber may also include a coating that extends along the fiber axis and terminates at a distal end. The coating may be a gold coating. The optical fiber may further include a second cladding that surrounds a portion of the coating along the fiber axis, and may terminate at a distal end. The optical fiber may also include an outer jacket that extends along the fiber axis and terminates at a distal end. The optical fiber may further include a fiber tip.

In a further example, a system may include an optical fiber. The optical fiber may include a fiber core that extends along a fiber axis. The fiber core may be configured to transmit a laser energy along the fiber axis and may terminate at a distal end. The optical fiber may further include a first cladding that extends along the fiber axis, is adjacent to the fiber core, and terminates at a distal end. The optical fiber may further include a coating that extends along the fiber axis and terminates at a distal end. The coating may be a gold coating. The optical fiber may further include a second cladding that surrounds a portion of the gold coating along the fiber axis, and terminates at a distal end. The optical fiber may also include an outer jacket that extends along the fiber axis and terminates at a distal end. The optical fiber may also include a fiber tip. The system may further include a laser source connected to the optical fiber.

Examples of the laser delivery device may include one or more of the following features. The kink radius of the optical fiber may be less than 8 mm. The device may include a braided liner surrounding the outer jacket. The braided liner may include a PTFE inner layer, a tungsten wire braided ultra-high molecular weight polyethylene layer, and an outer Pebax® layer. The device may include a slotted tube surrounding the outer jacket. The slotted tube may have a bend radius that decreases along the proximal-distal direction. The fiber tip may be a ball tip or flat tip. The fiber core may be a glass core. The first cladding may be a fluorinated glass cladding. The second cladding may include a dielectric material or a metallic material. The gold coating may be approximately 1-10 μm in thickness or thicker. The device may include an outer diameter of the outer jacket greater than an outer diameter of the second cladding, an outer diameter of the second cladding greater than an outer diameter of the gold coating, an outer diameter or the gold coating greater than the outer diameter of the cladding, and an outer diameter of the cladding greater than an outer diameter of the fiber core. The optical fiber may include a slotted tube or a braided liner. The kink radius of the optical fiber may be less than 2.5 mm. The device may have an outer diameter less than 2.3 mm. The length of the device along the fiber axis may be between 2 and 4 meters or longer. The optical fiber may be movable between a retracted position outside a patient's body and an extended position extending into the body of a patient.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

DETAILED DESCRIPTION

Aspects of the present disclosure are now described with reference to optical fibers and associated laser systems. Some aspects are described with reference to medical procedures where laser energy is used to treat a patient. References to a particular type of procedure, laser energy, and/or bodily organ are provided for convenience and not intended to limit the present disclosure unless claimed. Accordingly, the concepts described herein may be utilized for any analogous fiber—medical or otherwise.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements. Terms such as "generally," "about," "substantially," and/or "approximately" indicate a range of possible values that are within +/−5% of a stated value.

Figure 1:
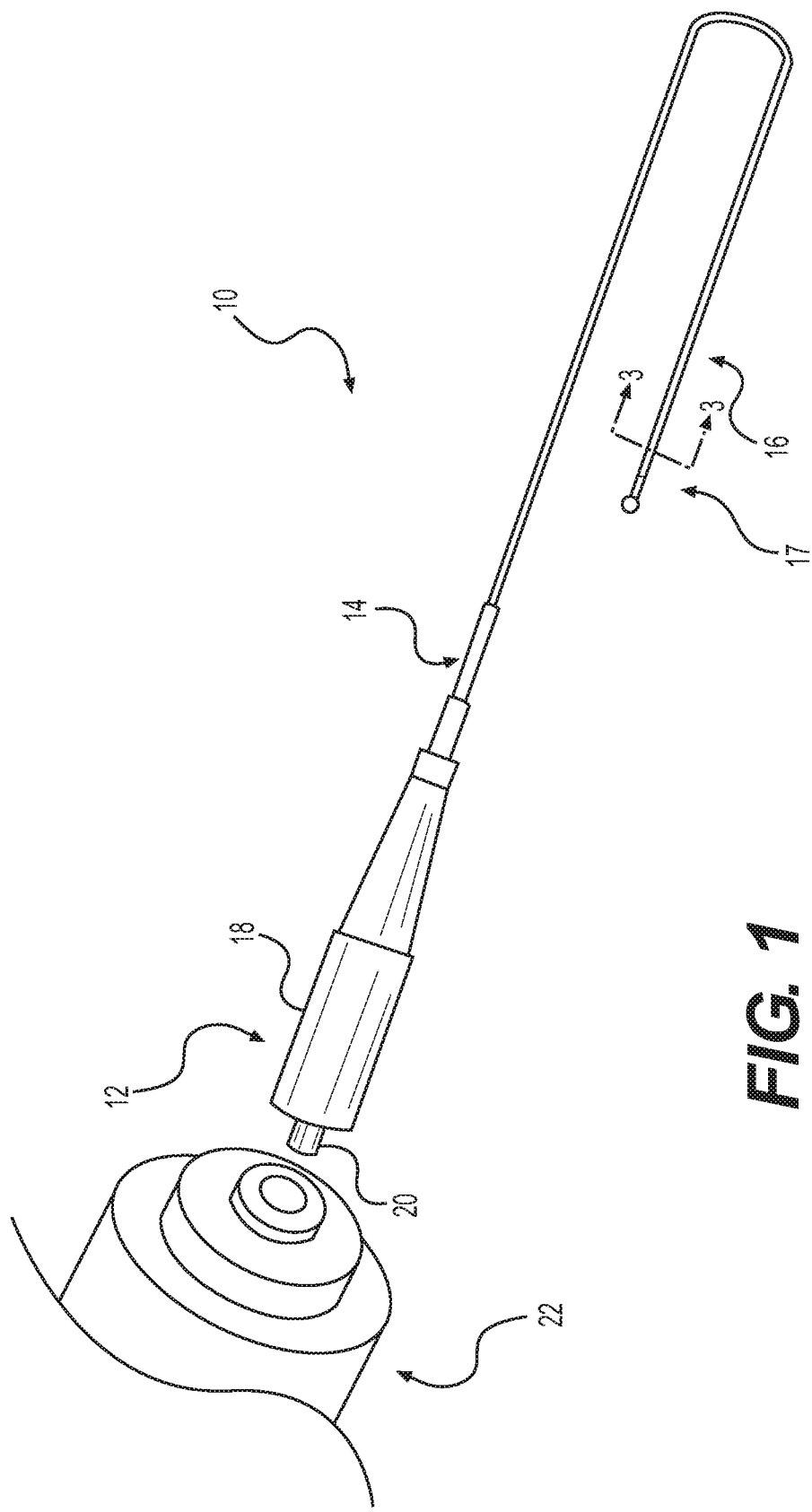
FIG. 1 illustrates an exemplary laser delivery device according to aspects of the present disclosure.

FIG. 1 illustrates a laser delivery device 10 with a proximal portion 12, an intermediate portion 14, and a distal portion 16 with a distal tip 17. Proximal portion 12 may include a handle 18 having a connector portion 20. Laser delivery device 10 may couple to a laser source 22 via connector portion 20 and transmit energy through an internal fiber in laser delivery device 10 and out of distal tip 17 to targeted material.

Laser source 22 may include a lens to narrow the laser energy, and may also include a port extending from laser housing to receive and mate with connector portion 20 of laser delivery device 10 in order to transmit laser energy through laser delivery device 10. Laser source 22 may be, for example, a holmium YAG (Ho:YAG) laser source emitting laser energy with a wavelength of approximately 2.1 μm and a power of approximately 100 W. Laser source 22 may generate laser energy with a shallow penetration depth of approximately 0.4 mm. In other aspects, laser source 22 may be a Thulium-doped YAG (Tm:YAG) laser source, a neodymium-doped YAG (Nd:YAG) laser source, a semiconductor laser diode, a potassium-titanyl phosphate crystal (KTP) laser source, or a Lithium Borate crystal (LBO) laser source. Laser source 22 may have a control module (not shown) to control a timing, a wavelength, and/or a power of the laser energy. The control module may control laser selection, filtering, temperature compensation, and/or Q-switching.

Connector portion 20 may be any type of SubMiniature version A ("SMA") connector or another appropriate optical fiber connector to mate with a port on the laser source 22. Connector portion 20 may include a central fiber to receive and transmit laser energy from laser source 22, and may also include an outer threading in order to be coupled to a port on the laser source 22. For example, connector portion 20 may be a male SMA connector, or connector portion 20 may be a female SMA connector.

As noted above, laser delivery device 10 may mate with laser source 22 through connector portion 20. Connector portion 20 may include an optical fiber and capillary or tube radially surrounding a proximal portion of the optical fiber. Optical fiber may extend through laser delivery device 10 from the connector portion 20 to the distal tip 17 to receive and transmit laser energy from laser source 22 to targeted material.

Figure 2:
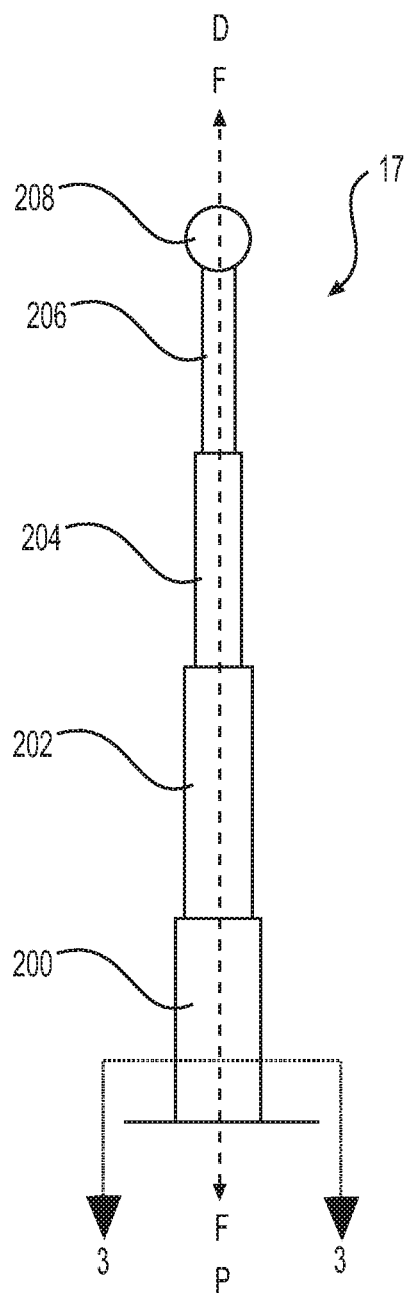
FIG. 2 depicts a distal end of the laser delivery device of FIG. 1 according to aspects of the present disclosure.

FIG. 2 illustrates the distal tip 17 of laser delivery device 10 extending along a fiber axis F-F and including layers comprising an outer jacket 200, a cladding 202, a coating 204, and a fiber 206; each partially removed in FIG. 2 to better illustrate the layers. The distal end of distal tip 17 is marked D and the proximal end is marked P in FIG. 2 signifying a proximal or distal direction along the fiber axis F-F. Note the term "distal end" does not necessarily mean distalmost end of a laser delivery device and may be any distal portion of the laser delivery device. The outer jacket 200, cladding 202, coating 204, and fiber 206 may extend longitudinally along the fiber axis from the proximal end to the distal end of the laser delivery device 10, and may have uniform or varied thickness. In some examples, laser delivery device 10 may have a maximum diameter of approximately 2.2 mm. In some aspects, laser delivery device 10 may have a length along the fiber axis F-F of 2-4 meters, and in other aspects may have a length along the fiber axis F-F of approximately 3 meters. Laser delivery device 10 may have a bend diameter of 1 mm, 2 mm, 3 mm, 4 mm, 5 mm, or up to 16 mm. In some examples, laser delivery device 10 may have a variable bend diameter. For example, laser delivery device 10 may have a decreasing bend diameter moving in the proximal-distal direction towards the distal tip 17. Bend diameter is the minimum diameter which laser delivery device will be bent to transmit laser energy without breaking the laser delivery device, and bend radius is the minimum radius which laser delivery device will be bent to transmit laser energy without breaking the laser delivery device.

As shown in FIG. 2, layers of laser delivery device 10 may be configured such that an outer diameter of outer jacket 200 is greater than an outer diameter of cladding 202; an outer diameter of cladding 202 is greater than an outer diameter of coating 204; and an outer diameter of coating 204 is greater than an outer diameter of fiber 206. In some examples, laser delivery device 10 may be described as tapering or stepping-down from a larger dimension to a smaller dimension in a proximal-to-distal direction along fiber axis F-F.

Outer jacket 200 may comprise one or more layers surrounding cladding 202, coating 204, and/or fiber 206 along fiber axis F-F. In some aspects, jacket 200 may be made of a polymeric material that is attached to cladding 202 along its length. Outer jacket may be any suitable material such as Polytetrafluoroethylene (PTFE), Nylon, polyvinyl chloride (PVC), low smoke zero halogen (LSFH) polymer, polyethylene (PE), polyurethane (PUR), polybutylene terephthalate (PBT), or polyamide (PA). In some aspects, outer jacket 200 may terminate at a distal end that is located proximal of a distal end of cladding 202, proximal of a distal end of coating 204, and/or proximal of a distal end of fiber 206. In other examples, outer jacket 200 may terminate at a distal end that is located at or proximate to the distal end of cladding 202, the distal end of coating, and/or the distal end of fiber 206. Outer jacket 200 may terminate at a distal end that is located at or proximate to fiber tip 208. In some aspects, outer jacket 200 may comprise a tube surrounding cladding 202, coating 204, and/or fiber 206; while in other aspects, outer jacket 200 may be a coating applied to cladding 202. In other examples, the outer jacket 200 may be omitted from laser delivery device 10.

Cladding 202 may comprise one or more layers surrounding coating 204 and/or fiber 206 along fiber axis F-F. In some aspects, cladding 202 may be a polymer cladding. In some aspects, cladding 202 may be made of a material that is dielectric, highly reflective, and/or biocompatible, such as a polymeric material. Cladding 202 may be made of glass, silica, plastic, or any other material. Cladding 202 may be configured to mechanically isolate coating 204 and/or fiber 206 from outer jacket 200, and/or further promote internal reflection of the laser energy. In some aspects, cladding 202 may comprise a tube surrounding fiber 206 and/or coating 204; while in others, cladding 202 may comprise a coating applied to coating 204. Cladding 202 may have a low refractive index and may have a lower refractive index than coating 204 and/or fiber 206. In some aspects, cladding 202 may have a lower density than coating 204 and/or fiber 206. Cladding 202 may cause light to be substantially confined within the laser delivery device 10 as light travels to the distal tip 17. Cladding 202 may terminate at a distal end that is located proximal of a distal end of coating 204 and/or proximal of a distal end of fiber 206. In other examples, cladding 202 may terminate at a distal end that is located at or proximate to the distal end of outer jacket 200, the distal end of coating 204, the distal end of fiber 206, and/or the fiber tip 208.

Coating 204 may comprise one or more layers surrounding fiber 206 along fiber axis F-F. Coating 204 may comprise a thin coating of gold applied to fiber 206 so that outer diameter of coating 204 is only nominally greater (e.g., 1% to 3%) than outer diameter of fiber 206. In some aspects, coating 204 may be approximately 3 μm thick, may be less than 3 μm thick, or may be greater than 1 μm and less than 3 μm thick. In some examples, coating 204 may be a gold coating, a silver coating, a mixture of gold and silver, copper coating, brass coating, or may be another metal coating. In other examples, coating 204 may be a highly reflective, low absorption coating, such a fused silica, or high reflection dielectric coatings. Coating 204 may terminate at a distal end that is located proximal of a distal end of fiber 206. In other examples, coating 204 may terminate at a distal end that is located at or proximate to the distal end of outer jacket 200, the distal cladding 202, the distal end of fiber 206, and/or at the fiber tip 208.

Figure 3:
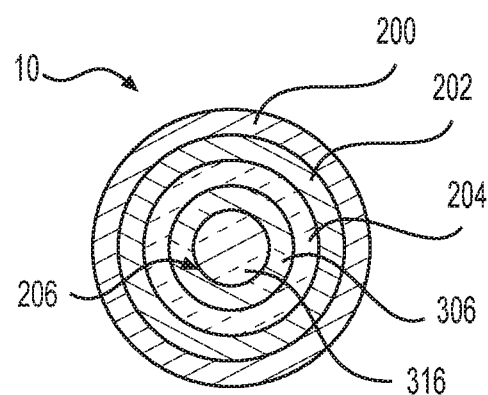
FIG. 3 depicts a cross-sectional view of the laser delivery device of FIG. 1 according to aspects of the present disclosure.

FIG. 3 shows a longitudinal cross-sectional view of laser delivery device 10 at section 3-3 shown in FIGS. 1 and 2. As shown in FIG. 3, fiber 206 may comprise a cladding 306 and a core 316. Fiber 206 may comprise one or more optical fibers configured to deliver laser energy and may be made of a suitable material to transmit laser energy. Fiber 206 may comprise a glass cladding and a glass core. Cladding 306 may surround portions of core 316, and may be fluorinated glass. In some examples, fiber 206 may comprise only a glass fiber core 316 without cladding 306. In other examples, core 316 may be made of any suitable material to transmit laser energy, such as, for example, silica with low or high hydroxyl (OH⁻) ion residual concentration. In some examples, the cladding 306 may be doped silica with, for example, fluorine. In some aspects, cladding 306 may be one or more cladding layers, may be a single or double cladding, and may be made of a hard polymer or silica.

Figure 4:
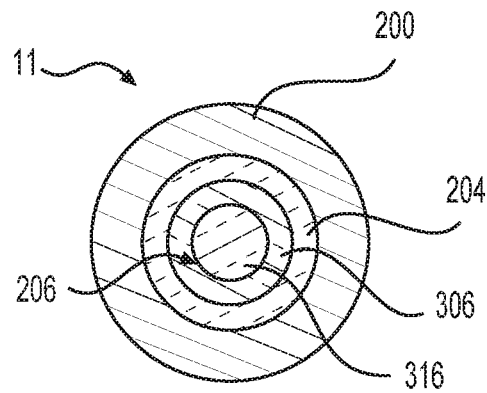
FIG. 4 depicts a cross-sectional view of a laser delivery device according to aspects of the present disclosure.

FIG. 4 shows a longitudinal cross-sectional view of another example of a laser delivery device 11 substantially similar to laser delivery device 10 except without cladding 202. Layers of laser delivery device 11 may be configured such that an outer diameter of outer jacket 200 is greater than an outer diameter of coating 204; and an outer diameter of coating 204 is greater than an outer diameter of fiber 206. In the same manner as the laser fiber of FIG. 3, fiber 206 of laser deliver device 11 may comprise a cladding 306 and a core 316.

The fiber tip 208 (shown in FIG. 2) of laser delivery device 10 may be a spherical end, a straight-firing end, a side-firing end, or another appropriate end. The fiber tip 208 of laser delivery device 10 emits laser energy toward the targeted material, so laser delivery device 10 serves as a waveguide for laser energy. Fiber tip 208 may be located at the distalmost point of laser delivery device 10. Laser energy may travel along fiber 206 from laser source 22 to fiber tip 208.

Figure 5:
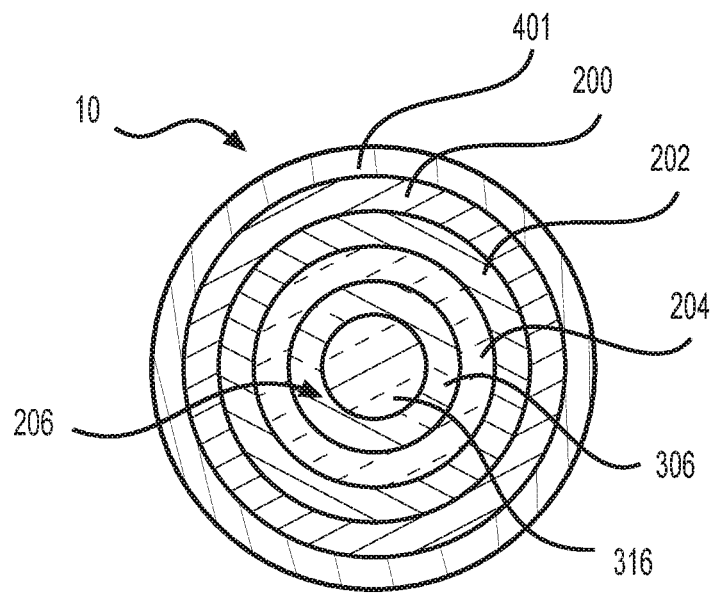
FIG. 5 depicts a cross-section view of an exemplary embodiment of a laser delivery device, according to aspects of the present disclosure.
Figure 6:
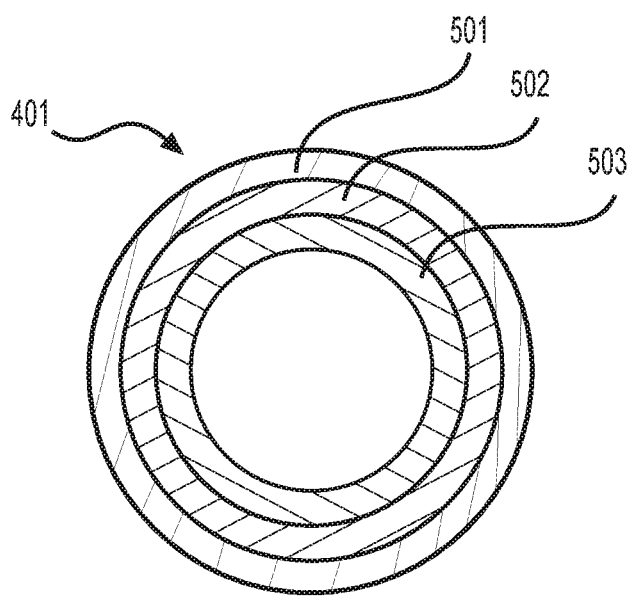
FIG. 6 depicts a cross-section view of an exemplary embodiment of a braided liner, according to aspects of the present disclosure.

In some examples, as shown in FIG. 5, laser delivery device 10 may comprise a braded liner 401 surrounding outer jacket 200, cladding 202, coating 204, and/or fiber 206 along fiber axis F-F. Braded liner may provide improved kink resistance to laser delivery device 10. Braded liner 401 may terminate at a distal end of laser delivery device 10 that is located proximal of a distal end of outer jacket 200, cladding 202, coating 204 and/or fiber 206. In other examples, braided liner may terminate at a distal end that is located at or proximate to the distal end of outer jacket 200, the distal end of cladding 202, the distal end of coating 204, the distal end of fiber 206, and/or the fiber tip 208. FIG. 6 shows a longitudinal cross-section of an exemplary braided liner 401 (with other layers of laser delivery device 10 omitted from the figure for clarity). Braided liner may include a polytetrafluoroethylene (PTFE) inner layer 503, a tungsten wire braided ultra-high molecular weight Polyethylene layer 502, and an outer Pebax® layer 501. In some examples, the PTFE inner layer may be laminated. Each layer of the braided liner may run longitudinally along the fiber axis F-F. In some aspects, the braided liner may be epoxy bonded to the next inner layer of the laser delivery device 10 at both the distal and proximal ends, or may be crimped to the next inner layer of the laser delivery device 10.

In other examples, as an alternative to the braided liner 401, laser delivery device 10 may comprise a slotted tube surrounding outer jacket 200, cladding 202, coating 204, and/or fiber 206 along fiber axis F-F. The slotted tube may be bonded, such as epoxy bonded, to outer jacket 200 and may increase kink resistance of the laser delivery device 10. In other examples, the slotted tube may be crimped to the outer layer of laser delivery device 10 or to outer jacket 200. In some examples, the slotted tube may have a smaller bending diameter at the distal end of the tube than at the proximal end of the tube. Slotted tube may have increasing slot density moving from the proximal to distal direction along the longitudinal axis of the tube.

Laser delivery device 10 may operate by transmitting laser energy from laser source 22 through connector 20 and through fiber 206 to the distal tip 17 of laser delivery device 10, where laser energy may be emitted from fiber tip 208 towards targeted tissue of a patient. Laser energy may be substantially contained within laser delivery device 10 between connector 20 and fiber tip 208. In some examples, laser deliver device 10 may be inserted through a working channel of an endoscope for transmission of laser energy through the laser delivery device 10 and the endoscope for application to a treatment site.

The various embodiments of the laser delivery device 10 may allow decreased kink radius and bend radius in an optical fiber while maintaining high transmission of light. Including a coating, such as a gold coating, may effectively increase transmission levels when a laser fiber is bent several times in succession. The design of the disclosed laser delivery device 10 may facilitate application of laser fibers in microcatheters and enable increased torque response of microcatheters utilizing laser fibers. Furthermore, the disclosed laser delivery device 10 may allow for improved transmission of laser fibers in catheters, particularly for use in embolization of blood vessels and similar procedures.

While principles of the present disclosure are described herein with reference to a laser delivery device, it should be understood that the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description. For example, while certain features have been described in connection with various embodiments, it is to be understood that any feature described in conjunction with any embodiment disclosed herein may be used with any other embodiment disclosed herein.

The invention claimed is:

1. A laser delivery device comprising:
   a fiber that extends along a fiber axis, wherein the fiber is configured to transmit a laser energy along the fiber axis, and terminates at a distal end of the fiber;
   a gold coating that extends along the fiber axis and terminates at a distal end of the coating, wherein the gold coating is applied on the fiber;
   a cladding that surrounds a portion of the gold coating along the fiber axis and terminates at a distal end of the cladding;
   an outer jacket that extends along the fiber axis and terminates at a distal end of the outer jacket;
   a fiber tip; and
   a liner surrounding the outer jacket.

2. The laser delivery device of claim 1, wherein a diameter of the gold coating is 1% to 3% greater than a diameter of the fiber.

3. The laser delivery device of claim 1, wherein the gold coating includes a thickness of less than 3 μm.

4. The laser delivery device of claim 3, wherein the thickness is between 1-3 μm.

5. The laser delivery device of claim 1, where the cladding is a second cladding and the fiber further comprises a first cladding and a core.

6. The laser delivery device of claim 5, wherein an outer diameter of the outer jacket is greater than an outer diameter of the gold coating, the outer diameter of the gold coating is greater than the outer diameter of the first cladding, and the outer diameter of the first cladding is greater than the outer diameter of the fiber core.

7. The laser delivery device of claim 5, wherein the fiber core is a glass core.

8. The laser delivery device of claim 5, wherein the first cladding is a fluorinated glass cladding.

9. The laser delivery device of claim 1, wherein the fiber tip is a ball tip.

10. The laser delivery device of claim 1, wherein the cladding includes a refractive index that is lower than a refractive index of the gold coating.

11. The laser delivery device of claim 1, wherein the cladding includes a dielectric material or a metallic material.

12. A laser delivery device, comprising:
    a connector portion at a proximal end of the laser delivery device; and
    an optical fiber connecting the connector portion to a distal end of the laser delivery device, wherein the optical fiber comprises:
       an inner fiber that extends along a fiber axis, wherein the inner fiber is configured to transmit a laser energy along the inner fiber axis, and terminates at a distal end of the inner fiber;
       a coating that extends along the inner fiber axis and terminates at a distal end of the coating, wherein the coating is a gold, silver, copper, or brass coating, and the coating is applied onto the inner fiber;
       a cladding that surrounds a portion of the gold coating along the fiber axis and terminates at a distal end of the cladding;
       an outer jacket that extends along the fiber axis and terminates at a distal end of the outer jacket; and
       a liner surrounding the outer jacket.

13. The laser delivery device of claim 12, wherein a bend radius of the laser delivery device is less than 8 mm.

14. The laser delivery device of claim 12, wherein a bend radius of the optical fiber is less than 2.5 mm.

15. The laser delivery device of claim 12, wherein the laser delivery device has an outer diameter less than 2.2 mm.

16. The laser delivery device of claim 12, wherein the liner comprises a braided liner.

17. A system comprising:
    an optical fiber comprising:
       an inner fiber that extends along an inner fiber axis, is configured to transmit a laser energy along said fiber axis, and terminates at a distal end of the inner fiber;

a gold coating that extends along the fiber axis and terminates at a distal end of the coating, wherein the gold coating is applied to a surface of the inner fiber;

a cladding that surrounds a portion of the gold coating along the fiber axis and terminates at a distal end of the cladding;

an outer jacket that extends along the fiber axis and terminates at a distal end of the outer jacket;

a fiber tip; and a liner surrounding the outer jacket.

18. The system of claim 17, wherein the cladding is a second cladding and the inner fiber further comprises a first cladding and a core.

19. The system of claim 18, wherein an outer diameter of the outer jacket is greater than an outer diameter of the second cladding, the outer diameter of the second cladding is greater than an outer diameter of the gold coating, the outer diameter of the gold coating is greater than the outer diameter of the first cladding, and the outer diameter of the first cladding is greater than the outer diameter of the fiber core.

\* \* \* \* \*